United States Patent
Bottke et al.

(10) Patent No.: US 7,230,141 B2
(45) Date of Patent: Jun. 12, 2007

(54) METHOD FOR PRODUCING TOLUOL DERIVATIVES

(75) Inventors: Nils Bottke, Mannheim (DE); Rolf-Hartmuth Fischer, Heidelberg (DE); Thomas Nöbel, Maxdorf (DE); Markus Rösch, Oppenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 236 days.

(21) Appl. No.: 10/500,718

(22) PCT Filed: Jan. 20, 2003

(86) PCT No.: PCT/EP03/00488

§ 371 (c)(1),
(2), (4) Date: Jul. 6, 2004

(87) PCT Pub. No.: WO03/062174

PCT Pub. Date: Jul. 31, 2003

(65) Prior Publication Data

US 2005/0032627 A1 Feb. 10, 2005

(30) Foreign Application Priority Data

Jan. 24, 2002 (DE) ................ 102 02 837

(51) Int. Cl.
*C07C 41/18* (2006.01)
*C07C 43/205* (2006.01)
(52) U.S. Cl. ............. 568/648; 568/650; 568/651; 568/652; 568/653; 568/658; 568/717; 568/772; 568/799
(58) Field of Classification Search ........ 568/648, 568/650, 651, 652, 653, 658, 717, 772, 799
See application file for complete search history.

(56) References Cited

U.S. PATENT DOCUMENTS 2,682,562 A * 6/1954 Wender et al. ............ 568/658
4,464,482 A   8/1984 Bird et al. ................. 502/325

FOREIGN PATENT DOCUMENTS

DE   904 529    2/1954
EP   606 072    7/1994
FR   678954     4/1930

OTHER PUBLICATIONS

Database, Crossfire Beilstein, XP002235170 Comptes Rendus Hebdomadaries des Seances de L'Academie des Sciences, vol. 172, 1921, pp. 735 Gauthier-Villars.
Alder et al. Justus Liebigs Annalen der Chemie, (1976), 1435-1447.
Krafft et al. Journal of Organic Chemistry, vol. 51, No. 26, 1986, pp. 5482-5484, XP002235169.
Ueda et al. Chem. Pharm. Bull., vol. 23, 2223-2231 (1975).
J. Am. Chem. Soc., vol. 79, Jan. 1957, 179-184, Goodwin et al.
Nightingate et al. J. Org. Chem. 1949, 14, 1089-1093.
Ranade et al. Chem. Eur. J. (2000), vol. 6(2), 313-320.
Synthesis, vol. 8, 797-802, 1993, Merz et al.
Pincock et al. Journal of Organic Chemistry., vol. 59, No. 19, 1994, pp. 5587, 5595, XP002235171.

* cited by examiner

Primary Examiner—Rosalynd Keys
(74) Attorney, Agent, or Firm—Novak Druce & Quigg, LLP

(57) ABSTRACT

A process for preparing toluene derivatives of the formula I,

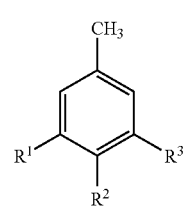

where $R^1$, $R^2$ and $R^3$ independently of one another are hydrogen, halogen, $C_1$–$C_6$-alkyl, hydroxyl or $C_1$–$C_6$-alkoxy, by hydrogenating benzaldehydes and/or benzyl alcohols of the formula II,

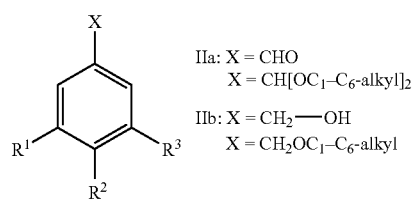

IIa: X = CHO
    X = CH[$OC_1$–$C_6$-alkyl]$_2$
IIb: X = $CH_2$—OH
    X = $CH_2OC_1$–$C_6$-alkyl with hydrogen in the presence of a catalyst, which is described in more detail in the description.

12 Claims, No Drawings

METHOD FOR PRODUCING TOLUOL DERIVATIVES

The present invention relates to a process for preparing toluene derivatives I,

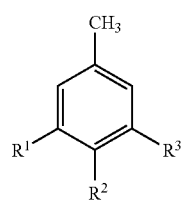

where $R^1$, $R^2$ and $R^3$ independently of one another are hydrogen, halogen, $C_1$–$C_6$-alkyl, hydroxyl or $C_1$–$C_6$-alkoxy, by hydrogenating benzaldehydes and/or benzyl alcohols of the formula II,

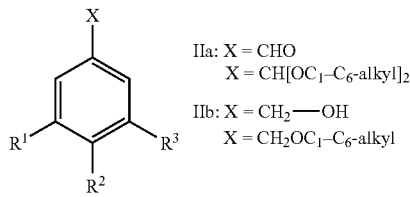

IIa: X = CHO
X = CH[OC$_1$–C$_6$-alkyl]$_2$

IIb: X = CH$_2$—OH
X = CH$_2$OC$_1$–C$_6$-alkyl with hydrogen in the presence of a catalyst.

The catalytic hydrogenation of benzaldehydes or benzlyl alcohol II to give the corresponding toluene derivatives I is known in principle from the literature.

Synthesis, Volume 8 (1993), page 799 discloses hydrogenating 3,4,5-trimethoxybenzaldehyde, dissolved in acetic acid, in the presence of 10% palladium on activated carbon to give 3,4,5-trimethoxytoluene.

According to Liebigs Annalen der Chemie 1976, Issue 7/8, page 1445, in a similar manner syringaldehyde (4-hydroxy-3,5-dimethoxybenzaldehyde) is hydrogenated in the presence of 10% palladium on activated carbon, also in glacial acetic acid, to give 4-hydroxy-3,5-dimethoxytoluene.

The Journal of American Chemical Society Volume 79 of 1957, pages 179–184 describes the hydrogenation of 3,4,5-trimethoxybenzyl alcohol in glacial acetic acid in the presence of palladium on activated carbon (10%).

Disadvantages of all of the abovementioned processes are that water formed in the reaction forms, together with acetic acid, a corrosive solvent mixture, and that an expensive noble metal is used as hydrogenation catalyst.

EP 606072 reports the hydrogenation of benzaldehydes in the presence of shaped titanium oxide containing a platinum group metal. The starting materials are used in an only 1% strength aqueous or ethanolic solution and thus at high dilution. The hydrogenation proceeds with low yield and extremely low selectivity. Byproducts which occur are nuclear-hydrogenated and demethylated benzenes.

For the hydrogenation of p-methoxybenzyl alcohol to give p-methoxytoluene, according to J. Org. Chem., 1949, 14, page 1089, copper chromite catalysts and, as solvent, methanol are used. The direct conversion of p-methoxybenzaldehyde to p-methoxytoluene is merely mentioned in general, however, without being verified by an example. A disadvantage of this process is the use of chromium-containing catalysts.

The hydrogenation of benzyl alcohols is further described in Chem. Eur. J. (2000), 6 (2), pages 313–320. Expensive noble metal catalysts are used, such as rhodium on carbon or rhodium on an $Al_2O_3$ support which produce in addition a high proportion of nuclear-hydrogenated products.

It is an object of the present invention to develop a process for preparing substituted toluene compounds which can be carried out with high yield and selectivity and avoids said disadvantages. In the process, especially, expensive noble metal catalysts, chromium-containing catalysts and corrosive solvents should be avoided. Side reactions such as the nuclear hydrogenation to give cyclohexane derivatives, the decarbonylation of the aldehyde function or the elimination of substituents such as alkoxy or halogen at the phenyl ring should be prevented as completely as possible.

We have found that this object is achieved by a process for preparing toluene derivatives of the formula I,

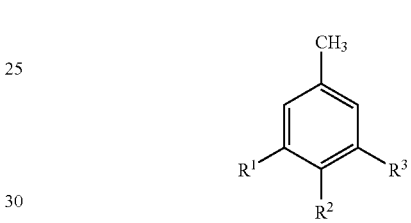

where $R^1$, $R^2$ and $R^3$ independently of one another are hydrogen, halogen, $C_1$–$C_6$-alkyl, hydroxyl or $C_1$–$C_6$-alkoxy, by hydrogenating benzaldehydes and/or benzyl alcohols of the formula II,

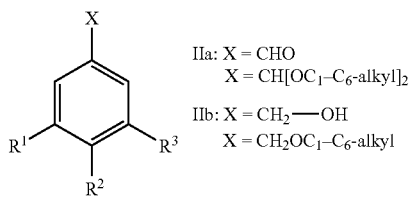

IIa: X = CHO
X = CH[OC$_1$–C$_6$-alkyl]$_2$

IIb: X = CH$_2$—OH
X = CH$_2$OC$_1$–C$_6$-alkyl with hydrogen in the presence of a catalyst, which comprises the catalyst having the following composition:

(a) at least one metal and/or at least one oxide, hydroxide or salt of a metal selected from the group consisting of cobalt, nickel and copper;

(b) from 0 to 50% by weight of one or more metals and/or one or more oxides, hydroxides or salts of a metal selected from the group consisting of platinum, rhodium, iron, silver, molybdenum, tungsten, manganese, rhenium, zinc, cadmium, lead, aluminum, zirconium, tin, phosphorus, silicon, arsenic, antimony, bismuth, titanium and rare earth metals, and (c) from 0 to 5% by weight of an alkali metal oxide or alkaline earth metal oxide, alkali metal hydroxide or alkaline earth metal hydroxide, or alkali metal salt or alkaline earth metal salt, where the sum of the components (a) to (c), provided that a support is not additionally used, is 100% by weight.

A possible embodiment of the catalyst comprises:

(a) from 40 to 99% by weight, based on the sum of the components (a)–(c) of one or more metals and/or one or more oxides, hydroxides or salts of metals selected from the group consisting of cobalt, nickel and copper;

(b) from 0.1 to 40% by weight, based on the sum of the components (a)–(c), of one or more metals and/or oxides, hydroxides or salts of metals selected from the group consisting of platinum, rhodium, iron, silver, molybdenum, tungsten, manganese, rhenium, zinc, cadmium, lead, aluminum, zirconium, tin, phosphorus, silicon, arsenic, antimony, bismuth, and rare earth metals, and (c) from 0.05 to 5% by weight, based on the sum of the components (a)–(c) of one or more alkali metal oxides or alkaline earth metal oxides, alkali metal hydroxides or alkaline earth metal hydroxides or alkali metal salts or alkaline earth metal salts.

Some preferred embodiments are described below, the preferences in each case applying for a single component and also for a combination of differing components. The quantities given below are based on the sum of the components (a)–(c). Any support which may be present has not been taken into account in these figures.

Preferred catalysts are those in which the component (a) makes up from 5 to 100% by weight. Those which are preferred in particular are catalysts which contain component (a) at from 40 to 99% by weight.

In addition, catalysts are preferred in which the component (b) is present at from 0 to 50% by weight, and in particular at from 1 to 40% by weight.

Preferred catalysts contain as component (b) at least one oxide, hydroxide or salt of a metal selected from the group consisting of platinum, rhodium, iron, silver, molybdenum, tungsten, manganese, rhenium, zinc, cadmium, lead, aluminum, zirconium, tin, phosphorus, silicon, arsenic, antimony, bismuth, and rare earth metals.

Particularly preferred catalysts contain as component (b) at least one oxide, hydroxide or salt of a metal selected from the group consisting of aluminum, silicon, zirconium, molybdenum, manganese and phosphorus.

The component (c) used in the inventive catalysts is preferably oxides or salts of alkali metals and alkaline earth metals selected from the group consisting of lithium, potassium, cesium, magnesium and calcium, and in particular preferably sodium.

The starting materials which can be used are in particular compounds of the formulae IIa and IIb individually or as mixtures, where $R^1$ to $R^3$ have the abovementioned meaning and $R^4$ is hydrogen or $C_1$–$C_6$-alkyl. In some cases it has proved advantageous to use the aldehydes IIa in the form of their acetals. The acetals may be prepared from the aldehydes IIa by reacting them with a $C_1$–$C_6$-alcohol using methods conventional in the literature.

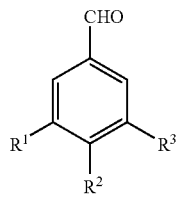

IIa

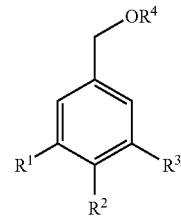

IIb

The catalysts can be used as homogeneous catalysts in dissolved form or as heterogeneous catalysts. The heterogeneous catalysts can be supported catalysts, solid catalysts or Raney catalysts which are used in fixed-bed, suspended or turbulent form. Suitable support materials are, for example, oxides such as aluminum oxide, silicon dioxide, alumino silicates, lanthanum oxide, titanium dioxide, zirconium dioxide, magnesium oxide, zinc oxide and zeolites, and activated carbon or mixtures thereof.

The heterogeneous catalysts are generally prepared in such a manner that precursors of the components (a), optionally together with precursors of the components (b) (promoters) and/or optionally together with precursors of the trace components (c) are precipitated in the presence or absence of support materials (depending on which catalyst type is wanted), and optionally the resultant catalyst precursors are processed into rods or tablets, dried and then calcined. Supported catalysts are generally also obtainable by impregnating the support with a solution of the components (a) and optionally (b) and/or (c), the individual components being able to be added simultaneously or successively, or by spraying the components (a) and optionally (b) and/or (c) onto the support by methods known per se. If necessary, binders can be used in the production of the catalyst.

Suitable precursors of components (a) are generally readily water-soluble salts of the abovementioned metals such as nitrates, chlorides, acetates, formates and sulfates, preferably nitrates.

Suitable precursors of components (b) are generally readily water-soluble salts or complex salts of the abovementioned metals such as nitrates, chlorides, acetates, formates and sulfates, preferably nitrates.

Suitable precursors of the components (c) are generally readily water-soluble salts of the abovementioned alkali metals and alkaline earth metals such as hydroxides, carbonates, nitrates, chlorides, acetates, formates and sulfates, preferably hydroxides and carbonates.

Precipitation generally proceeds from aqueous solutions, optionally by adding precipitation reagents, by changing the pH or by changing the temperature.

Usually the resultant catalyst precursor composition is pre-dried at temperatures in the range from 80 to 150° C., preferably from 80 to 120° C.

The calcination is customarily performed at temperatures in the range from 150 to 500° C., preferably from 200 to 450° C., in a gas stream of air or nitrogen.

If appropriate the catalyst surface is passivated, which is customarily carried out at temperatures in the range from 20 to 80° C., preferably from 25 to 35° C., using oxygen/nitrogen mixtures such as air.

The resultant calcined and possibly passivated catalyst composition is generally exposed to a reducing atmosphere ("activation"), for example by exposing it to a gas stream which comprises free hydrogen at a temperature in the range from 100 to 500° C., preferably from 150 to 400° C., for from 2 to 60 h. The gas stream preferably consists of from 20 to 100% by volume of hydrogen and from 0 to 50% by volume of an inert gas such as nitrogen.

From the preferred activation of the catalyst direct in the synthesis reactor, advantages for processing economics result.

The inventive catalysts are distinguished by high activity and make high throughputs possible at a virtually complete conversion rate.

The hydrogenation can be carried out batchwise, but in particular continuously. In the case of continuous operation, the hydrogenation can be carried out in the bottom phase or in the trickle procedure, in the gas phase or in the liquid phase.

The starting materials of the formulae IIa and IIb are accessible by the processes described in the literature cited at the outset.

The compounds IIa and IIb can be hydrogenated without solvent, for example in the gas phase or as melt. In some cases it has proved to be advantageous to add a solvent.

Suitable solvents are those which have sufficient dissolving power for the starting materials II and the target products I and which are stable under the hydrogenation conditions. Examples of such solvents are ethers such as tetrahydrofuran, dioxane, tetrahydropyran, polyethylene glycol dialkyl ethers or polyethylene glycol monoalkyl ethers, water, alcohols such as methanol, ethanol, tert-butanol, cyclohexanol, alkylbenzenes such as toluene or xylenes, phenols such as pyrocatechol, resorcinol, hydroquinone, pyrogallol or alkyl ethers of these phenols. Mixtures thereof can also be used.

Preferred solvents are tetrahydrofuran, dioxane, tetrahydropyran, polyethylene glycol dialkyl ethers, polyethylene glycol monoalkyl ethers, alkylbenzenes, water and alcohols or mixtures of these compounds. Those which are suitable in particular are ethers or ether/water mixtures. Also preferred are alcohols and alcohol/water mixtures, in particular methanol and methanol/water mixtures.

A solution from 1 to 60% strength by weight, for example, of the starting materials II in said solvents is hydrogenated.

In a preferred embodiment, the hydrogenation is carried out in the gas phase without using a solvent.

Hydrogenation is performed at temperatures of from optionally 20 to 280° C. and pressures of from optionally 1 to 300 bar, preferably at temperatures from 100 to 260° C. and pressures of from 20 to 250 bar.

The hydrogen used for the hydrogenation is generally used in relatively great stoichiometric excess relative to the starting compound II.

It can be recycled to the reaction as recirculated gas. The hydrogen used is generally of technical grade purity. Admixtures of inert gases, for example nitrogen, do not interfere with the course of the reaction, however.

The compounds I which can be prepared by the inventive hydrogenation are valuable intermediates which can be used to prepare drugs, fine chemicals and plant protection compounds.

The invention is described in more detail below with reference to examples. The percentages are percentages by weight.

Examples of Inventive Catalysts:
catalyst A: 60% by weight CuO; 40% by weight $Al_2O_3$;
catalyst B: 65.4% by weight CoO; 20.2% by weight CuO; 8.3% by weight $Mn_3O_4$; 3.5% by weight $MoO_3$; 2.4% by weight $P_2O_5$; 0.2% by weight $Na_2O$;
catalyst C: 74.0% by weight NiO; 2.2% by weight $MoO_3$; 23.8% by weight CuO; on $ZrO_2$ as support;
catalyst D: 77.7% by weight NiO, 13.6% by weight $SiO_2$, 5.8% by weight $Al_2O_3$, 4.7% by weight $ZrO_2$.

Activation of Catalyst A

In an electrically heatable reactor, 50 g of catalyst A, through which passed a nitrogen stream of 100 l(S.T.P.)/h, were heated to 250° C. starting from room temperature. For the following 12 h, 5 l(S.T.P.)/h of hydrogen were added to the nitrogen stream. In the course of the next 5 h, the nitrogen was then replaced by pure hydrogen.

Activation of Catalysts B, C and D at Atmospheric Pressure

After charging an electrically heatable reactor of 1 liter in capacity with the catalyst, at a nitrogen stream of 300 l/h, the temperature was increased hourly by approximately 20° C. starting from room temperature, until 290° C. was reached. Then, in the course of 6 hours, the nitrogen was replaced by hydrogen. For this, hourly the hydrogen content was increased by 50 l/h and at the same time the nitrogen content decreased by 50 l/h. When 300 l/h hydrogen feed is reached, the reactor temperature was increased to 300–310° C. and kept for 48 hours at 300 l/h hydrogen. The catalyst was removed after cooling under argon and stored under tetraethylene glycol dimethyl ether.

Preparation of Toluene Derivatives of the Formula I

EXAMPLE 1

Hydrogenation of 3,4,5-trimethoxybenzaldehyde in the Gas Phase in the Presence of Copper Catalysts The experiment was carried out in a gas phase apparatus, consisting of an evaporator, a reactor and a condenser. The starting compound was vaporized in the evaporator on Raschig rings in a counterflow stream of hydrogen. The hydrogen stream saturated with the starting compound was brought to reaction on the already preactivated catalyst. The gas stream is then passed into a condenser from which the products which passed into the liquid state could be drained off. The hydrogen pressure in the hydrogenation apparatus was 1 bar during the reaction.

4.5 g of 3,4,5-trimethoxybenzaldehyde were evaporated per hour on Raschig rings in the counterflow stream of hydrogen and passed over 50 g of preactivated catalyst A at a temperature of 260° C. The hydrogen/starting material ratio (mol/mol) was approximately 4:1. At a conversion rate of 94%, a selectivity of 85% was achieved.

EXAMPLE 2

Hydrogenation of 3,4,5-trimethoxybenzaldehyde in the Liquid Phase in the Presence of Nickel Catalysts 1 g of catalyst D in a catalyst basket insert was placed in a 300 ml pressure reactor and 10 g of 3,4,5-trimethoxybenzaldehyde in 100 g of methanol were added. The hydrogenation was carried out using pure hydrogen at a constant pressure of 200 bar and a temperature of 180° C. Hydrogenation was continued until hydrogen was no longer absorbed. The reactor was then depressurized. The aldehyde conversion rate was 100%. The yield of the desired toluene derivative was 91%, based on the total amount of aldehyde used.

EXAMPLE 3

Hydrogenation of 3,4,5-trimethoxybenzaldehyde in the Liquid Phase in the Presence of Cobalt Catalysts In a similar manner to Example 2, 10 g of 3,4,5-trimethoxy-benzaldehyde dissolved in 100 g of tetrahydrofuran were hydrogenated in the presence of 1 g of catalyst B. The aldehyde conversion rate was 100%. The yield of the desired toluene derivative was 96%, based on the total amount of aldehyde used.

EXAMPLE 4

Hydrogenation of a Melt of 3,4,5-trimethoxybenzaldehyde in the Liquid Phase

In a similar manner to Example 2, 10 g of 3,4,5-trimethoxy-benzaldehyde were hydrogenated without solvent in the presence of 1 g of catalyst C. The aldehyde conversion rate was 100%. The yield of the desired toluene derivative was 94%, based on the total amount of aldehyde used.

What is claimed is:

1. A process for preparing toluene derivatives of the formula I,

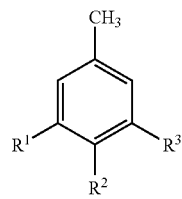

where R1, R2 and R3 independently of one another are hydroxyl or C1–C6-alkoxy, by hydrogenating benzaldehydes and/or benzyl alcohols of the formula II,

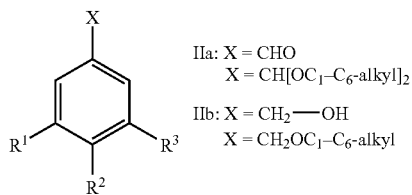

IIa: X = CHO
X = CH[OC$_1$–C$_6$-alkyl]$_2$

IIb: X = CH$_2$—OH
X = CH$_2$OC$_1$–C$_6$-alkyl with hydrogen in the presence of a catalyst, wherein the catalyst consists essentially of a catalytically active constituent and optionally a support material, and the catalytically active constituent consists essentially of:

(a) at least one metal and/or at least one oxide, hydroxide or salt of a metal selected from the group consisting of cobalt, nickel and copper;

(b) from 0 to 50% by weight of one or more metals and/or one or more oxides, hydroxides or salts of a metal selected from the group consisting of platinum, rhodium, iron, silver, molybdenum, tungsten, manganese, rhenium, zinc, cadmium, lead, aluminum, zirconium, tin, phosphorus, silicon, arsenic, antimony, bismuth, titanium and rare earth metals, and (c) from 0 to 5% by weight of an alkali metal oxide or alkaline earth metal oxide, alkali metal hydroxide or alkaline earth metal hydroxide, or alkali metal salt or alkaline earth metal salt, where the sum of the weight percentages of components (a) to (c) is 100% by weight wherein the catalyst is a heterogeneous catalyst.

2. A process as claimed in claim 1, wherein the component (a) makes up from 40 to 99% by weight of the sum of the components (a) to (c).

3. A process for preparing toluene derivatives of the formula I,

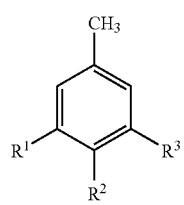

where R1, R2 and R3 independently of one another are hydroxyl or C1–C6-alkoxy, by hydrogenating benzaldehydes and/or benzyl alcohols of the formula II,

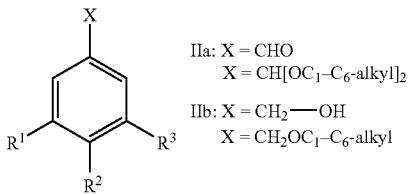

IIa: X = CHO
X = CH[OC$_1$–C$_6$-alkyl]$_2$

IIb: X = CH$_2$—OH
X = CH$_2$OC$_1$–C$_6$-alkyl with hydrogen in the presence of a catalyst, wherein the catalyst consists essentially of a catalytically active constituent and optionally a support material, and the catalytically active constituent consists essentially of:

(a) at least one metal and/or at least one oxide, hydroxide or salt of a metal selected from the group consisting of cobalt, nickel and copper;

(b) from 0 to 50% by weight of one or more metals and/or one or more oxides, hydroxides or salts of a metal selected from the group consisting of platinum, rhodium, iron, silver, molybdenum, tungsten, manganese, rhenium, zinc, cadmium, lead, aluminum, zirconium, tin, phosphorus, silicon, arsenic, antimony, bismuth, titanium and rare earth metals, and (c) from 0 to 5% by weight of an alkali metal oxide or alkaline earth metal oxide, alkali metal hydroxide or alkaline earth metal hydroxide, or alkali metal salt or alkaline earth metal salt, where the sum of the weight percentages of components (a) to (c) is 100% by weight, wherein the component (b) makes up from 1 to 40% by weight of the sum of the components (a) to (c).

4. A process for preparing toluene derivatives of the formula I,

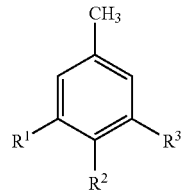

where R1, R2 and R3 independently of one another are hydroxyl or C1–C6-alkoxy, by hydrogenating benzaldehydes and/or benzyl alcohols of the formula II,

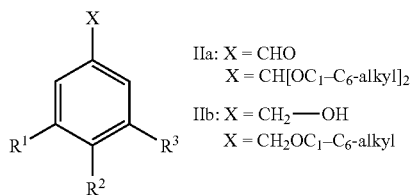

IIa: X = CHO
X = CH[OC$_1$–C$_6$-alkyl]$_2$
IIb: X = CH$_2$—OH
X = CH$_2$OC$_1$–C$_6$-alkyl with hydrogen in the presence of a catalyst, wherein the catalyst consists essentially of a catalytically active constituent and optionally a support material, and the catalytically active constituent consists essentially of:
(a) at least one metal and/or at least one oxide, hydroxide or salt of a metal selected from the group consisting of cobalt, nickel and copper;
(b) from 0 to 50% by weight of one or more metals and/or one or more oxides, hydroxides or salts of a metal selected from the group consisting of platinum, rhodium, iron, silver, molybdenum, tungsten, manganese, rhenium, zinc, cadmium, lead, aluminum, zirconium, tin, phosphorus, silicon, arsenic, antimony, bismuth, titanium and rare earth metals, and
(c) from 0 to 5% by weight of an alkali metal oxide or alkaline earth metal oxide, alkali metal hydroxide or alkaline earth metal hydroxide, or alkali metal salt or alkaline earth metal salt,
where the sum of the weight percentages of components (a) to (c) is 100% by weight, wherein the component (c) makes up from 0.05 to 5% by weight of the sum of the components (a) to (c).

5. A process as claimed in claim 1 wherein the hydrogenation is carried out in a solvent.

6. A process as claimed in claim 5, wherein the solvent is an ether, an alkylbenzene, water or alcohol or a mixture thereof.

7. A process as claimed in claim 1, wherein the hydrogenation is carried out in the gas phase.

8. A process as claimed in claim 1 wherein the hydrogenation is carried out in the melt of compound II.

9. A process as claimed in claim 1, wherein the hydrogenation is carried out at pressures of from 20 to 250 bar and at temperatures of from 100 to 260° C.

10. A process as claimed in claim 1 for preparing 3,4,5-trimethoxytoluene.

11. The process of claim 1, wherein the catalytically active constituent has the following composition:
(a) at least one metal and/or at least one oxide, hydroxide or salt of a metal selected from the group consisting of cobalt, nickel and copper;
(b) from 0 to 50% by weight of one or more metals and/or one or more oxides, hydroxides or salts of a metal selected from the group consisting of platinum, rhodium, iron, silver, molybdenum, tungsten, manganese, rhenium, zinc, cadmium, lead, aluminum, zirconium, tin, phosphorus, silicon, arsenic, antimony, bismuth, titanium and rare earth metals, and
(c) from 0 to 5% by weight of an alkali metal oxide or alkaline earth metal oxide, alkali metal hydroxide or alkaline earth metal hydroxide, or alkali metal salt or alkaline earth metal salt, and the sum of the components (a) to (c) is 100% by weight.

12. The process of claim 1, wherein the catalyst comprises at least one support material selected from the group consisting of aluminum oxide, silicon dioxide, alumino silicates, lanthanum oxide, titanium dioxide, ziconium dioxide, magnesium oxide, zinc oxide, zeolites and activated carbon.

* * * * *